US007112806B2

(12) United States Patent
Lussier

(10) Patent No.: US 7,112,806 B2
(45) Date of Patent: Sep. 26, 2006

(54) BIO-IMAGING AND INFORMATION SYSTEM FOR SCANNING, DETECTING, DIAGNOSING AND OPTIMIZING PLANT HEALTH

(76) Inventor: Robert Lussier, One Piper Rd., Lexington, MA (US) 02421

( * ) Notice: Subject to any disclaimer, the term of this patent is extended or adjusted under 35 U.S.C. 154(b) by 121 days.

(21) Appl. No.: 10/255,225

(22) Filed: Sep. 26, 2002

(65) Prior Publication Data

US 2005/0072935 A1    Apr. 7, 2005

Related U.S. Application Data

(60) Provisional application No. 60/325,345, filed on Sep. 27, 2001.

(51) Int. Cl.
*G01N 21/64* (2006.01)
(52) U.S. Cl. .............................. 250/458.1; 250/461.1; 250/459.1
(58) Field of Classification Search ............. 250/458.1, 250/459.1, 461.2, 461.1; 356/317, 318, 417
See application file for complete search history.

(56) References Cited

U.S. PATENT DOCUMENTS

| 4,018,530 | A | * | 4/1977 | Hirschfeld | ................... 356/317 |
| 5,014,225 | A | * | 5/1991 | Vidaver et al. | ............... 702/19 |
| 5,130,545 | A | * | 7/1992 | Lussier | ..................... 250/458.1 |
| 5,567,947 | A |   | 10/1996 | Kebabian | |
| 5,843,680 | A | * | 12/1998 | Manian et al. | ............... 435/7.4 |
| 6,563,122 | B1 | * | 5/2003 | Ludeker et al. | .......... 250/458.1 |
| 6,573,512 | B1 | * | 6/2003 | Oberlin et al. | ............ 250/458.1 |
| 2003/0146394 | A1 | * | 8/2003 | Prange et al. | ............ 250/458.1 |
| 2005/0114801 | A1 | * | 5/2005 | Yang et al. | .................. 715/961 |

OTHER PUBLICATIONS

Lichtenthaler, H; Vegetation Stress: an Introduction to the Stress Concept in Plants; Jplant Phys., 148, 4-14, ('96).
McMurtrey JE, Chappelle EW; Distinguishing Nitrogen Levels in Field Corn with Actively Induced Fluorescence and Passive Reflectance Measurements; Remote Sensing Environ. 47-36-44 ('94).
Albers B., DiBenedetto J., More Efficient Environmental Monitoring with Laser-Induced Fluorescence Imaging; Biophotonics Int., Nov./Dec. '95.

* cited by examiner

*Primary Examiner*—Otilia Gabor
*Assistant Examiner*—Christine Sung
(74) *Attorney, Agent, or Firm*—Brian M. Dingman; Mirick, O'Connell, DeMallie & Lougee

(57) ABSTRACT

A portable Chlorophyll Fluorescence Imaging Time (CFIT) system for use in determining plant health. The system includes an enclosure for placement around a plant to be imaged in-situ. There is a controlled light source that controllably provides to the plant light of a desired wavelength range, to controllably irradiate the plant within the enclosure. The chlorophyll fluorescence emitted from the plant both spatially and temporally is captured, and the captured fluorescence information is analyzed to provide plant health information.

15 Claims, 5 Drawing Sheets

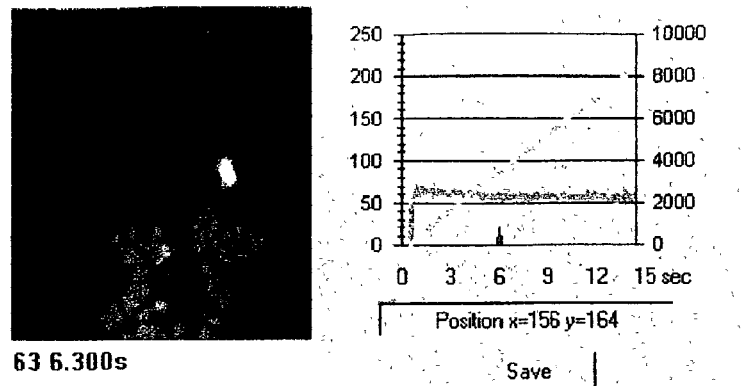
FIG. 4A  Excellent Photosynthetic Efficiency; graphic measures Fc and no Ftransient. Tomato sample.
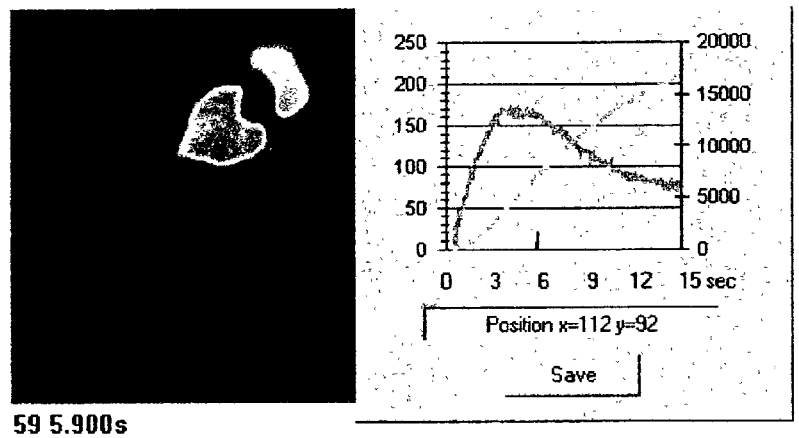
FIG. 4B  Early Bean drought stress.
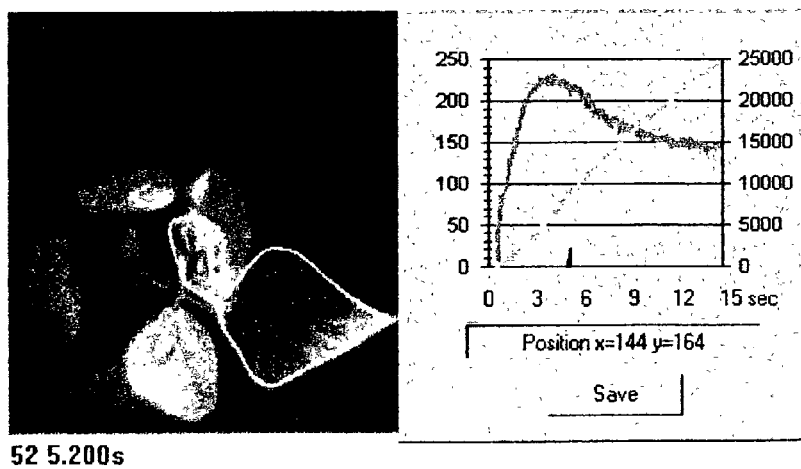
FIG. 4C  Advanced Stress, bean drought

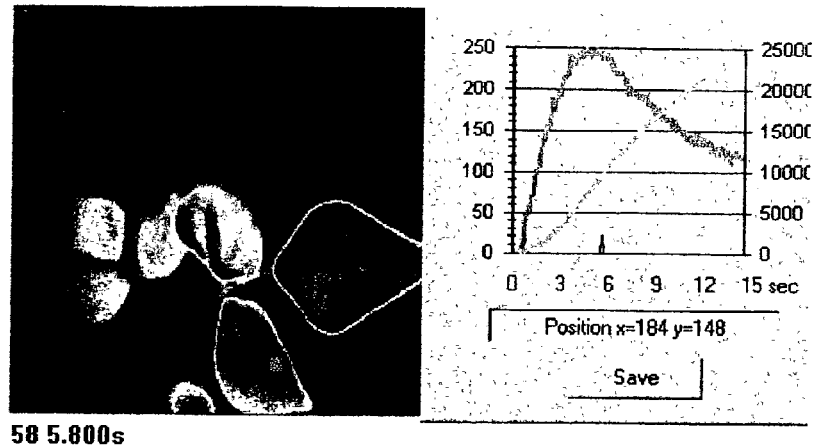
FIG. 4D Advanced Stress; Bean Drought 7-16-01; plant watered after test.
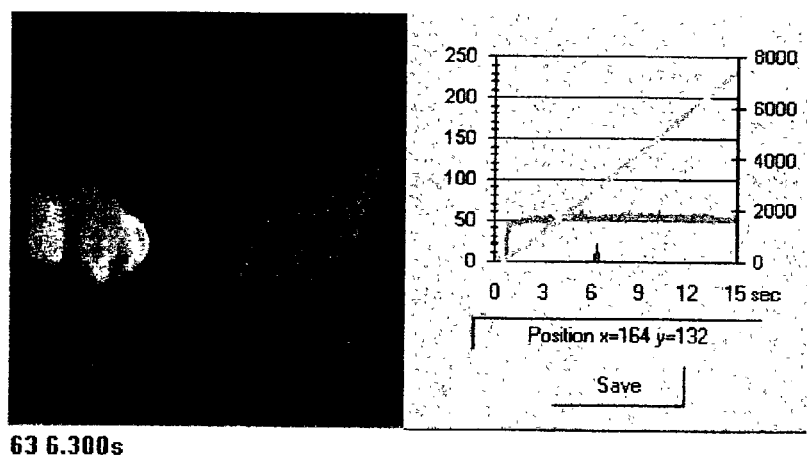
FIG. 4E Bean drought test; above plant 24 hrs after water.

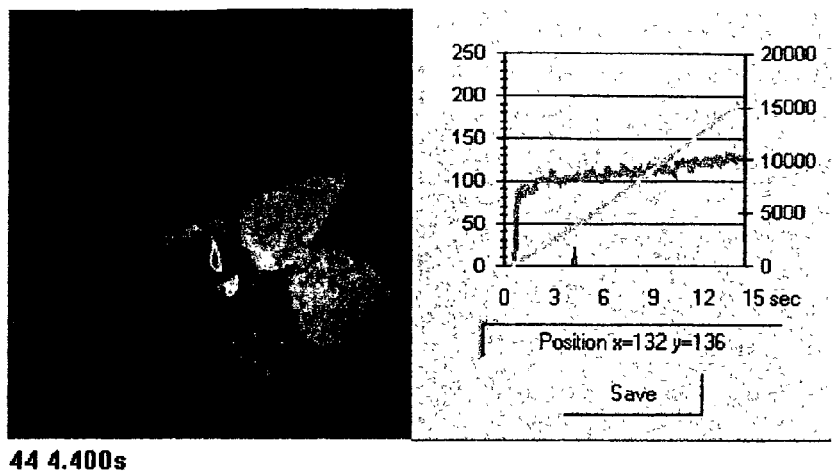
FIG. 4F Same Plant after another 24 hrs, indicating thermal stress.

BIO-IMAGING AND INFORMATION SYSTEM FOR SCANNING, DETECTING, DIAGNOSING AND OPTIMIZING PLANT HEALTH

CROSS REFERENCE TO RELATED APPLICATION

This application claims priority of Provisional application Ser. No. 60/325,345, filed on Sep. 27, 2001.

FIELD OF THE INVENTION

This invention relates to an imaging system for inspecting and determining the status of plant health with the early detection, diagnosis and quantification of plant stress responses that indicate nutrient deficiency or disease in plants from either the environment or from pathogens and in so doing, manages and optimizes the photosynthetic efficiency and growth and yield in plants.

BACKGROUND OF THE INVENTION

Plant health and growth is affected by the chlorophyll pigments and their relationship to photosynthesis in plants. Plants are green because the chlorophyll pigments reflect visible green light and absorb blue and red light from the visible light spectrum. The photon absorbed energy is passed on to two photosynthetic reaction centers, Photosystem II (PSII) and Photosystem I (PSI). The photon absorbed energy in PSII has three competing uses; (1) the increase of photon energy extracts hydrogen electrons from water releasing oxygen to the atmosphere. The electron transport is used to increase photochemistry in the form of photosynthetic chemicals ATP and NADPH which react with absorbed carbon dioxide to produce carbohydrate for the growth and yield of plants; (2) some of the absorbed energy is also emitted in the form of heat and is not part of the photosynthetic process and (3) a low amount of absorbed photon energy is emitted in the form of chlorophyll fluorescence in the red spectral region. These competing uses result in the following. If photochemistry and/or non-photosynthetic heat are active for absorbed energy, fluorescence will be low. If they are inactive, then fluorescence will be high. This simplified description of photosynthesis and the inverse relationship of fluorescence to photosynthetic efficiency has had considerable detailed study in the past. Researchers have sought to detect plant stress responses by measuring the emitted fluorescence and the photosynthesis relationship with the use of various instruments for applications in biology, agriculture and ecology.

The important universal parameter that relates photosynthetic efficiency and health in plants is the yield and lifetime of chlorophyll pigments which absorb light energy in certain visible spectral bands and, as chlorophyll fluorescence, emit part of this energy at longer wavelengths in the far-red and near-infrared spectral regions. Chlorophyll fluorescence will increase if the chlorophyll-absorbed energy exceeds the plant's immediate photosynthetic activity or efficiency. In general, the magnitude of fluorescence emission is inversely proportional to the photosynthetic efficiency of the plant. The fluorescence emission is also an indicator that is directly proportional to the concentration of chlorophyll (yield) in the plant leaf.

Monitoring plant fluorescence emissions provides the opportunity to monitor plant health. A low emission is normal in healthy plants. Abnormal increased fluorescence emissions are caused by external plant stress stimuli that decrease photosynthetic activity or efficiency or damage photosynthesis pathways. If the stress condition is removed, and no photosynthetic damage has resulted, the plant will acclimate to an Early Stress stage and even recover from an Advance Stress stage. If the stress condition continues unabated, the deterioration of photosynthesis will continue and extend to a Critical Stress stage, with the first visible indication (color change or wilt) of photosynthetic pathway damage and a non-recoverable plant stress condition. This disrupts the photosynthesis process where the yield and quanta of chlorophyll molecules decreases, exacerbating the condition to the Lethal stage with extreme visible symptoms) and causes plant death.

Plant stress pressures may be caused by pathogens including worms or viral, bacterial and fungal disease, or from environmental causes including temperature, water drought, chemicals or industrial effluents. Other stressors may be due to plant metabolism and physiological changes due to under-fertilization or over-fertilization. The fate of chlorophyll, i.e. its yield and lifetime, must be taken into account when monitoring plant health and the physiological response to plant stress conditions.

A low-cost measure of early plant stress remains the key objective of laboratory research or ground-based systems for commercial grower application. In most cases, a measurement of chlorophyll is the basis on which a determination of stress is made. Simple metering devices may use solar reflectance or active light to measure chlorophyll fluorescence at a sensitive spectral wavelength and compare it to the fluorescence at a second wavelength outside the region of sensitivity. However, these metering methods do not account for fluorescence changes due to the natural variable distribution of chlorophyll fluorescence (located interveinal) or that caused by the plant stress condition. The plant stress condition will vary, so that the fluorescence emission is not uniformly distributed on plants or plant leaves. Fluorescence usually begins at the outer rim of a leaf and on the upper leaves where more photosynthetic activity is located. A limitation of present metering instruments is the inability to spatially locate the varied distributed emission for accurate measurement.

Airborne and satellite remote sensing of vegetation first used passive solar reflectance to measure chlorophyll changes. When plants are measured with a suitable radiometer, the blue reflectance (450–480 nm) and red reflectance (620–700 nm) will be slight, the green reflectance (500–550 nm) will increase and the near infrared reflectance will be greater. The changes are due to the absorption of light by the chlorophyll pigments. Any physiological stress, disease, nutrient or reduced amount of photosynthetic pigments causes an increase in the blue and red reflectance and a substantial decrease in the near infrared reflectance. Data obtained from various spectral ranges and developed as ratios such as NIR/R and NIR−R/NIR+R have been used as vegetation indices to assess plants from airborne or satellite remote sensing platforms. Changes in these ratios can be a relative estimate of stress when data from different areas of the field are compared, even if the specific cause for the stress cannot be identified.

An important limitation of solar passive reflectance is the variation in solar radiation in one location due to atmospheric conditions and/or sun angle and/or that caused by plant orientation. The plant's diurnal changes due to transpiration in the morning are a cause of additional water stress. High humidity, and the presence of dew on leaves, also influence the spectral reflectance. The spectral signature is also influenced by the amount of pigments, leaf angle, leaf texture, the physiological factors of stress, and the plant growth stage. These limitations account for the number of different vegetation indices and relate to the difficulty in correlating a spectral ratio number to the broad range of plant vegetation response.

The remote sensing of vegetation exhibits sharp reflectance changes in the 690–740 nm range. This phenomenon has encouraged the use of narrow-band, multi-spectral radiometry to isolate the two signatures for plant stress response. The analysis of red reflectance, (690 nm), and the ratio of red to NIR reflectance, (690/740), has been shown to be responsive to the status of chlorophyll in the vegetation canopy and in individual plants.

To improve the chlorophyll measurements and remove the limitations of reflectance measurements, ground-based systems have sought the use of active light sources. Active chlorophyll fluorescence measurements use actinic (photosynthetic active) light sources to induce the kinetics of electron transport and to measure chlorophyll fluorescence. Filtered light sources of low wavelength pass-band in the near UV or visible range discriminate the low-level, fluorescence signals from out-of-band noise, and with Fabry-Perot interference filters, detect and improve the resolution for specific chlorophyll fluorescence signatures, usually in the NIR. Laser Induced Fluorescence (LIF) methods use laser light as the light source in a number of science studies. McMurtrey and Chappelle describe LIF using laser light in the NUV (355 nm) to irradiate plants and detect fluorescence signatures at blue, 440 nm; green, 520 nm; red, 690 nm and far-red, 740 nm. The ratios of 690/740, 690/520 and 690/440 are used to determine plant stress in the field (in-situ). Laser Induced Fluorescence Imaging (LIFI) studies by DOE use a laser light source with a line-scan imager to detect chlorophyll fluorescence imaging for sensing with airborne helicopter at night for the detection and measure of induced plant stress (arsenic). Lichtenthaler et al use LIFI to measure the same ratios of non-chlorophyll and chlorophyll fluorescence values at 440/690 or 440/740 to determine plant stress. LIFI methods, with high frequency, high energy NUV lasers, remain a deterrent for commercial application to consumers and non-scientific users.

The measure of low-level chlorophyll fluorescence in the field is difficult in daylight unless the plants or leaf parts are shrouded from ambient light scatter. To overcome this limitation, researchers have sought means to provide a better measure of fluorescence in the field. McFarlane et al described a Fraunhofer line discriminator using 656 nm to measure chlorophyll fluorescence in wet vs. dry water stress in trees. Fraunhofer lines are observed as dark spectral lines of solar light indicating their opacity due to the absorbance by gases in the sun's or earth's atmosphere. The line at 656 nm is due to hydrogen absorption in the solar atmosphere. The Fraunhofer A, B lines at 686 nm and 759 nm are due to the absorption by oxygen in the earth's atmosphere and overlap the spectral bandwidth for the emission of chlorophyll fluorescence. When recording measurements from the vegetative canopy with a spectral detector such as a photomultiplier, the difference signal at the Fraunhofer center wavelength compared to the adjoining spectral band is chlorophyll fluorescence without any additional out-of-band noise-signal from light scatter. However, fluorescence can reflect and light scatter onto an adjacent plant leaf. To assure that the fluorescence measurements of a single plant leaf are correct, a caveat requires that the plant being measured must be isolated and not affected by the fluorescence/reflectance emission of adjacent plants or leaves.

Kebabian in U.S. Pat. No. 5,567,947 cites the use of Fraunhofer wavelengths at 690 nm and 760 nm to measure chlorophyll fluorescence emissions from vegetative canopy. The Fraunhofer lines, due to the absorption by oxygen in the earth's atmosphere, will eliminate noise from out-of-band light scatter in these bands, leaving only chlorophyll fluorescence and the in-band emissions from the canopy. The method focuses light from the vegetation canopy with a lens and narrow-band filters as input to a quartz tube of oxygen in a spherical cavity, and measures a delayed, secondary emission of oxygen fluorescence at 760 nm that is proportional to the fluorescence/reflected light levels from the vegetative canopy.

In the above references, a simple ratio of reflectance or chlorophyll fluorescence tested in two spectral bands is used to detect the plant stress response. However, single number ratios provide no additional information related to the temporal-related values of fluorescence emission to diagnose the plant stress damage stage.

Lussier in U.S. Pat. No. 5,130,545, describes a Video Plant Management System, using active Chlorophyll Fluorescence Imaging from absorbed light, 400 to 600 nm, with NIR video to image and record the time-dependent chlorophyll fluorescence signatures to detect plant stress. The system uses dark-adapted plants and shutters light to induce transient fluorescence emission (the Kautsky Effect and chlorophyll fluorescence quenching) that is directly attributed to photosynthetic electron transport and energy transfer in the plant's chloroplast cells. The method uses video data (frames per second) to record visually and temporally the time dependent fluorescence emitted to determine the plant's physiological response to disease and plant stress. The method uses a delayed timing to image and measure the chlorophyll fluorescence intensity across a leaf with a line scan, and records the temporal changes of the line scan according to the video rate.

SUMMARY OF THE INVENTION

This invention emphasizes new techniques with chlorophyll fluorescence imaging and time-related fluorescence signatures for evaluating plant stress responses and photosynthesis pathways using multi-spectral video imaging with computer-based image, data and information processing. The invention's Chlorophyll Fluorescence Imaging method using sensitive video resolves spatially where the fluorescence emission is maximized on the plant, and processes the pixels at that location to more accurately measure the fluorescence-intensity-time parameters of the plant stress condition.

This invention features a portable Chlorophyll Fluorescence Imaging Time (CFIT) system for use in determining plant health. The system includes an enclosure for placement around a plant to be imaged in-situ. There is a shuttered light source that controllably provides to the plant light of a desired wavelength range, to controllably irradiate the plant within the enclosure. The chlorophyll fluorescence emitted from the plant both spatially and temporally is captured, and the captured fluorescence information is analyzed.

The invention comprises an improved laboratory-bench or portable field Chlorophyll-Fluorescence Imaging Temporal (CFIT) system with near-infrared video to image and quantify chlorophyll fluorescence for real-time detection and diagnosis of plant stress with computer processed Fluorescence-Intensity-Time (FIT) graphics and image-data files. The laboratory/field system uses active light to shutter and irradiate dark-adapted plants in a light-tight box that excludes ambient light and, with intensified CCD or CMOS video imager and computer processor, images, digitizes and processes the red and near-infrared chlorophyll fluorescence spectral bands of 690 and 740 nm to image, quantify and diagnose chlorophyll fluorescence photosynthetic efficiency, and plant stresses responses for real-time, laboratory and field management applications.

The laboratory/portable CFIT system uses an active light source for day-night operation, filtered for visible light in the spectral band of 400–650 nm. The active light source may be a mercury halide lamp with shutter, or switching off/on/off an array of light emitting diodes for active chlorophyll induction of the dark-adapted plants. The CFIT imager is an intensified CMOS or CCD silicon sensor array with digital video processing and, together with computer information processing, images and quantifies CFIT signatures with Fluorescence-Intensity-Time (FIT) graphics that measure the transfer of fluorescence energy and fluorescence quenching to detect and diagnose the early, advanced and critical stages of plant stress, the symptoms of which are not visible to the eye. With video imaging, information processing and database architecture, the invention records plant stresses as files that are stored in the computer database as a library of fluorescence signatures and/or plant stress responses for plant health evaluation by the user. The image processing auto-calibrates the system in real-time and removes the problem of balanced light variation. The algorithms and software for the calibration of light and the imaging, measure and diagnosis of plant stress are embedded in the computer application software program.

It is therefore an object of this invention to provide multi-spectral, pass-band filters with video imaging and information processing to image, quantify and diagnose plant stress and photosynthetic efficiency with time-dependent chlorophyll fluorescence imaging of plants and leaves (in situ) using improved analysis of plant photosynthesis responses that are processed as a video-image X-Y-T datacube and with additional spectral signatures and computer information processing, provides the calibration, database and management information for agricultural and environmental Users.

It is a further object of this invention to provide such a system that can be used to monitor and diagnose early plant stress in part of a plant or an entire plant in-situ in a field of plants, the greenhouse and garden.

It is further object of this invention to provide such a system that monitors plants in-situ for:
Pathogen stress
Temperature stress
Water stress (drought or excess)
Excess Light stress
Nutrient Deficiency (abnormal, inadequate fertilization) stress
Chemical Stress from herbicides, pesticides or growth regulators
Heavy Metals and other pollutants from industrial contamination.

It is a further object of this invention to monitor the photosynthetic efficiency, yield and growth-rate of plants.

It is a further object of this invention to provide management information of the plants in the laboratory/field to optimize photosynthetic efficiency, yield and growth-rate.

It is a purpose of this invention to define a new method of imaging, quantifying and diagnosing plant stress that achieves the following; 1) the measure of plant health and the early detection of plant stress response from external plant stress stimuli before damage symptoms become visible, 2) the graphical measure of the plant's physiological response to stress that diagnoses the period or time of recoverable early and advanced plant stress damage and of non-recoverable critical or lethal plant stress damage, 3) the imaging and indication of where the plant stress is spatially located on plant leaves, and 4) the imaging and quantification of plant health together with computer processing of management information in the database, enabling the user to manage solutions to improve and optimize plant health, growth and productivity.

To achieve these improvements, this invention adds the variable of time to the method of chlorophyll fluorescence imaging, to improve the means to quantify photosynthetic efficiency and diagnose real-time plant stress. The invention monitors the fate of chlorophyll with a system that spatially locates and quantifies the variable of chlorophyll fluorescence intensity over time that is expressed in photosynthesis as electron transport. The quantification of the variable time-constant of fluorescence also defines the measure and cumulative deterioration of photosynthetic efficiency as well as the diagnosis of early, advanced and critical plant stress over time. The measurement of these stresses or changes in photosynthetic efficiency may be expressed by graphics of fluorescence-intensity-time that directly quantify early, advanced, critical and lethal plant stress, and determine the plant's ability to recover or not recover from an external plant stress condition.

The invention extends the referenced Lussier method and measurement of TDF with Chlorophyll Fluorescence Imaging Time (CFIT) by using the entire video image to digitize, process and record the temporal changes of the induced chlorophyll fluorescence. The method uses a low-level intensified video imager, digitized video and computer information processing to capture the matrix x-y pixel array of the video frame, expanded over time to include n-video-frames to matrix an x,y,t image datacube. The computer software supports 1) a fluorescence-image-time datacube, 2) the means to interactively select and obtain a fluorescence-image-time graphic of any x,y,t location on the image data, 3) visualization means from the computer display of video imagery to image and detect the variable fluorescence intensity thresholds using false-colors, 4) user interactive processing to spatially locate and measure variable fluorescence intensity on plant leaves or whole plants, 5) computer scaling and processing to depict and graphically measure the fluorescence-intensity time with the first integral to add a more resolved measure of transient chlorophyll fluorescence intensity and quenching that diagnoses the cumulative status of plant stress deterioration; i.e. early and advanced recoverable plant stress; critical, non-recoverable plant stress (first visible symptoms) and lethal or extreme visible, damaged plant stress. With computer processing and its inherent archival capability, the method provides an image database for plant stress management and management information applications.

The CFIT method is advantageous in that it images chlorophyll fluorescence emissions to determine spatially where the plant stress is indicated on the leaf, then enables the user to interactively measure at the spatial x-y location in real-time the transient and variable chlorophyll fluorescence, photosynthetic efficiency or the plant's physiological response to plant stress and to diagnose the stages of stress. The invention has the further advantage to enable applications that include image processing, plant stress database and management information systems.

The CFIT system application software is described with macro definitions.

BRIEF DESCRIPTION OF THE DRAWINGS

Other objects features and advantages will occur to those skilled in the art from the following description of the preferred embodiment, and the accompanying drawings, in which:

FIGS. 4a–4f are a series of enhanced fluorescence images of plant portions juxtaposed with plots of fluorescence intensity versus time and the area under the fluorescence curve.

DETAILED DISCLOSURE OF THE PREFERRED EMBODIMENT

Figure 1:
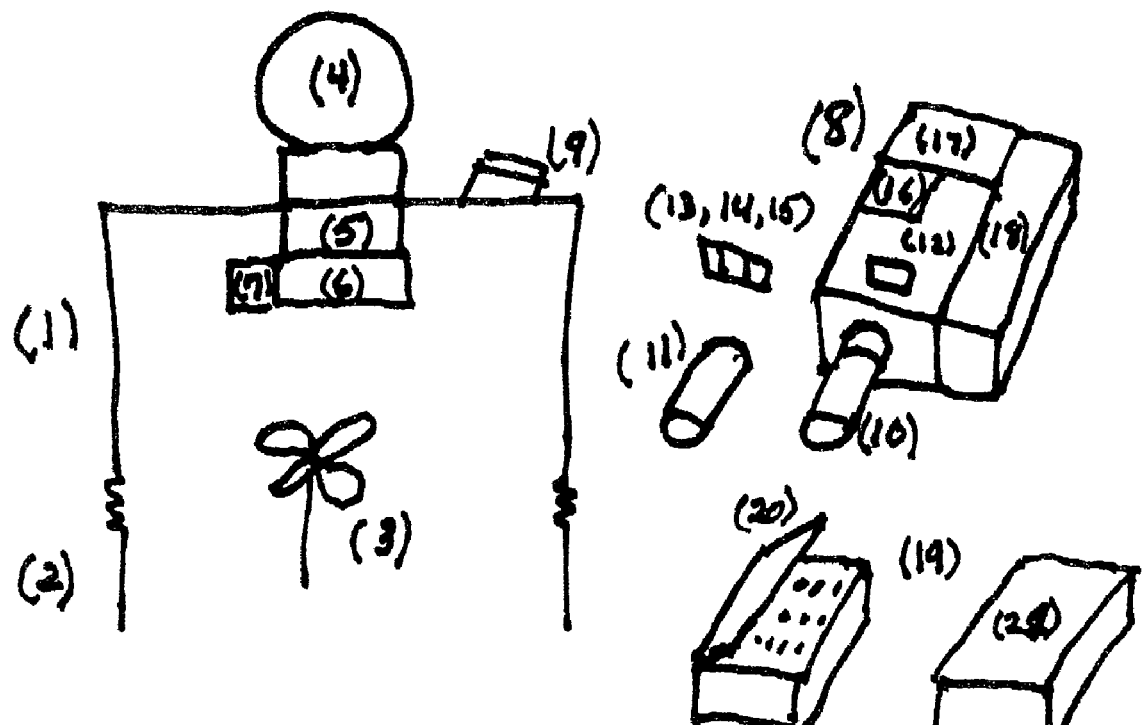
FIG. 1 is a highly schematic view of the preferred embodiment of the system of this invention.

As shown in FIG. 1, the CFIT System, a closed box (1), is inserted into closed-side extenders (2) to accommodate varying plant height and is placed over the test plant (3) so that the plant has no incident ambient light except for the active light source (4) from either a NUV mercury lamp or a mercury halogen lamp with continuous visible light or from an array of light emitting diodes with blue, and/or blue-green, yellow spectra. The active light source is irradiated on the low-pass-band filters (5) to limit the spectral pass-bands to NUV 230 to 400 or from VIS 400 to 650 nm or from 650 nm to 1100 mm depending on the operation required. The spectral light is obstructed by shutter (6) that is opened by the shutter actuator (7) under control of the computer information processor (19) with embedded control program software to illuminate and control the test program for the plant specimen. The plant's physiological response to any plant stress stimuli that is present or introduced, pathogen or environmental, is imaged, recorded and processed by the intensified CMOS or CCD silicon-based video imager (8) which is separate and attached through the bracket (9). The imager may operate with either a single or dual lens. Lens (10) is a close-up lens with photo-intensifier to image low-level fluorescence emissions in the closed-box operation day or night. A second lens can be used to enable a second narrow-spectral band, 740 nm, and/or integrates a photo-diode array with interference filters to capture additional reflective VIS/NIR narrow band signatures. The second lens may be replaced by lens (11), a telescopic lens for detecting reflective images on plants up to 10 meters or more in distance when the portable video imager is used independent of the field box to scan and detect reflective signatures indicative of stress in solar light. The lens components in lens 10 and lens 11 are physically changeable. The video image sensor area array (12) provides video operation in the usual manner. The narrow-band interference filters of 10 nm bandwidth limit incident light to 690 nm (13) to a single image sensor area array and to 740 nm (14) for a second, image sensor area array. A lens/photo-diode assembly with photo cells, filters (15) may replace lens 11 to measure reflective narrow-band VIS/NIR signatures to improve the diagnostic evaluation of the plant stress response. The optimal placement of the 690 and 740 nm interference filters is a position between the lens 10 and photo-intensifier. An alternative solution is to place filters (13), (14) and other filters together with a blank in a filter wheel in front of the lens 10 intensifier for the single video imager sensor area array (12) and with the computer information processor (20), control the selection of 690 nm, 740 nm, and other spectral bands. The embedded digital microprocessor (16) controls the operation of the shutter, filter wheel, photo-diode assembly and video imager and records the image file in computer RAM memory (17). The digital interface (18) delivers files to the external portable computer (19) and display (20) which controls all the operating software and test programs. The attached battery module (21) enables the portable operation of the field system.

Additionally, the CFIT method may be used to inspect plants at night with the above portable light source, imager and computer interface but without the confinement of the closed box. The advantage is to conduct a series of rapid plant stress measurements when all the plants are dark-adapted.

The CFIT method may also include an external device with full spectra lamp module 400–1000 nm and having fiber optic light guides attached to either side of a clamp on a leaf, enabling one to irradiate and detect NIR transmissive spectral bands through the plant leaf for the measure of carbohydrate, water, and chlorophyll transmissive spectral signatures which may be additionally used to diagnose and evaluate the causes of plant stress.

Alternatively, the CFIT method may also include an external device with full spectra lamp module 400–1100 nm, having fiber optic light guides attached to either side of a clamp on a leaf, enabling one to irradiate and detect VIS/NIR light reflected off the leaf or transmitted light through the leaf. The fiber optic detected light is focused on a photo-diode assembly where filters/photo cells measure the analog to digital values, under control of a microcomputer to determine the carbohydrate, water leaf moisture, and chlorophyll signatures as additional spectral information to evaluate the causes of plant stress.

The operation of the portable field system may be similarly conducted as a low-cost device by substituting a hand-held light source with an array of light emitting diodes or a lamp in 400–650 nm and focused by fiber optic light guides to a leaf clamp to detect fluorescence using a photo-diode array with Fabry-Perot filters for 690 and 740 nm to determine plant stress with the embedded microprocessor converting the analog photodiode array signals to CFIT digital values for display by the liquid crystal display (LCD).

Figure 2:
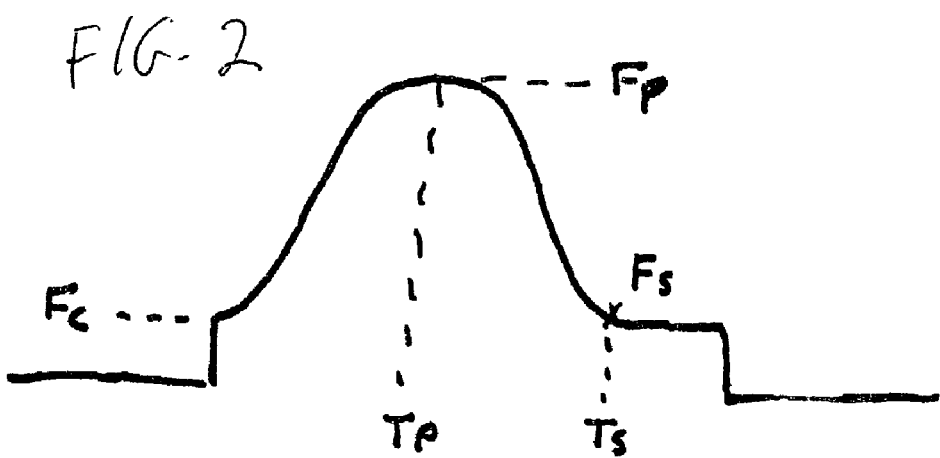
FIG. 2 is a graph of a typical chlorophyll fluorescence versus time curve for a healthy plant.
Figure 3:
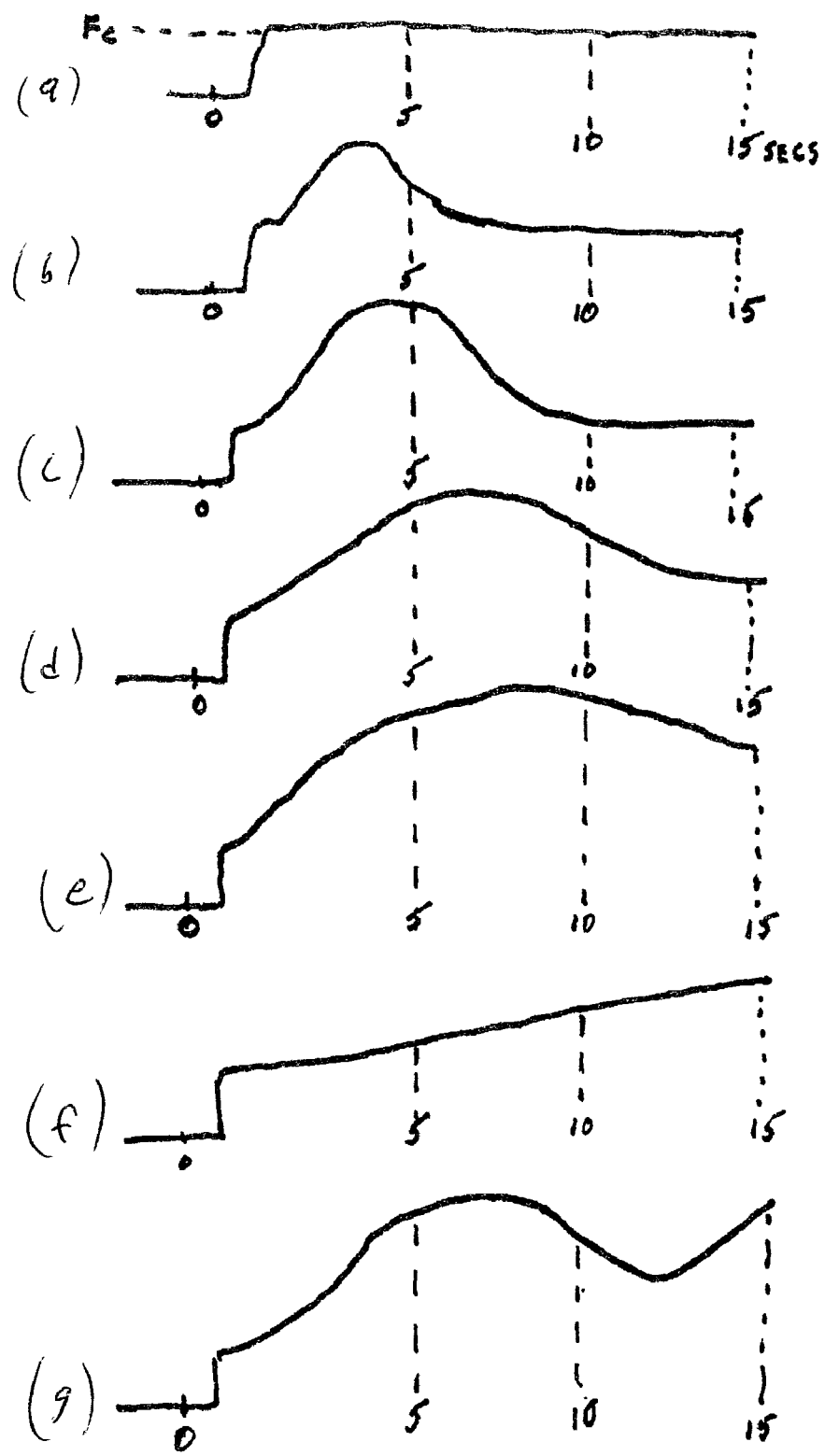
FIG. 3 is a series of curves of the type shown in FIG. 2 illustrating fluorescence response of plants with different types and levels of stress.

FIGS. 2–4 depict Chlorophyll Fluorescence Imaging Time signatures and their relationship to plant health, early plant stress and critical plant stress.

Operation

This invention results from the realization that a Laboratory-Bench CFIT system can extend to a dual field application with the imaging of whole plants and leaves in-situ to quantify time-dependent fluorescence signatures using active light for day-night operation and computer-processing for video imaging, image processing and information processing to image, detect, quantify and diagnose plant stress conditions. The modular, active light source may be used in either day or night operation. The invention uses a light-tight box to dark-adapt the plants and, with computer, shutters the visible spectral light with low band-pass filter for optimal chlorophyll absorption (400–650 nm), controls the intensified Video Imager (CMOS or CCD) with lens and narrow-band spectral filters at the sensor array, to digitize and capture, in real-time, the low-level digital imaging of the induced variable or transient chlorophyll fluorescence in the near infrared bandwidth of 690 nm–760 nm. The system visualizes the variable fluorescence-intensity thresholds with false colors to image plant stress signatures and, with interactive selection of the video x,y,t datacube and the spatial location of plant stress displayed on the leaf or leaves of whole plants in-situ, processes the Fluorescence-Intensity-Time graphic of the chlorophyll fluorescence imaging of time-dependent chlorophyll fluorescence and quenching signatures. The computer processes the CFIT signatures as the plant's physiological response to external plant stress stimuli and measures photosynthetic efficiency, chlorophyll-yield and plant stress to visualize, diagnose and record to the computer database the in-situ plant stresses as either: early recoverable stress, advance recoverable stress, critical non-recoverable stress or lethal non-recoverable stress (photosynthesis failure). The early and advance stress responses are not visible to the eye. As one example, the video imager and processor images, records and measures in 640×480 resolution at 10 frames/sec and 15 secs, 150 video frames to record the video x-y-t data-cube. The video datacube images, captures and digitizes the variable and temporal fluorescence, that is: Fsubv, initial fluorescence Fsubo, the chlorophyll yield Fsubc, the peak fluorescence intensity Fsubp at time tsubp, the quenching or relaxing of fluorescence to steady-state fluorescence, Fsubs, at time tsubs. These fluorescence variables enable the system to record, measure and diagnose in real-time the effects of external plant stress stimuli and to store the image-data to the computer for archival database and data management information.

The photosynthesis reaction is a three-step process; 1) light (photon) absorption by the chlorophyll pigments obtain higher energy levels to transfer hydrogen electrons and release oxygen from water and emit fluorescence (and heat); 2) the electron transport of displaced valence electrons to a higher energy level in PSII and PSI that lead to the photochemical formation of bio-chemicals ATP and NADPH and 3) the bio-chemical reactions with $CO_2$ that produce carbohydrates for plant growth. The chlorophyll fluorescence provides the emission signatures that characterizes the photosynthetic efficiency of the first two steps with the quantum energy yield of chlorophyll and the transport of electrons by acceptor-donors forming an electron-proton gradient at the cellular thylakoid and stroma membrane interface and the de-excitation of these electrons (quenching or recombination). The effect is fluorescence emission that is increased and delayed due to causes from external plant stress stimuli.

The CFIT low-level fluorescence emissions are imaged and recorded by a photo-intensified CMOS or CCD imager. The images are digitized within the imager or by a digital capture board in the computer processor under control of the processing software. In testing plant stress, it is necessary to dark-adapt the plant and reduce photosynthetic activity so that the chlorophyll pigments decrease to their low energy state. Dark adaptation time (DAT) varies with the plant species. A DAT of two-three minutes is typically sufficient to reduce photosynthetic activity to obtain a linear measurement of variable fluorescence. When the shutter is triggered open (computer-activated), the actinic light (which is always on) is instantly irradiated on the plant. The incident light induces fluorescence on the plant object. The fluorescence is measured by the CCD imager. The video stream captures the transient fluorescence intensity variation of the object plant image and a digital electronics or digital capture board converts the analog video to digital video images for each frame at the video frame rate. The image processing software auto-measures the light gain for each x-y pixel in the video frame and false colors the digital video images to visualize and threshold the fluorescence intensity values. In one example the colors are: the zero-level reference, black; low intensity, blue; medium intensity, white; high intensity, red; and high saturation level, green. The software processes and stores the digitized image-data into an x-y-t data matrix, a datacube of a video-frame image of x-y pixels and a video-stream of t video frames at the frame rate and recording time. The image-data file is stored by the software program temporarily in the computer's RAM memory and, if selected by the user as a standard or for comparison to other data files, the file is stored in disk memory and the image-file database. Conversely, any file of image-data can be recalled by the software from the computer image-file database.

After the imager records and processes the video image-data in memory, the CFIT software enables the user to interact with any selected frame and to place the computer cursor at any x-y pixel of the image-file. The software program converts the fluorescence intensity and time occurrence from the recorded x,y,t data-cube into a Fluorescence-Intensity-Time graphic, scaling and measuring fluorescence intensity on the left y-axis, time in seconds on the x-axis, and the first integral of intensity-time measure (the area under the curve) on the right y-axis.

The CFIT system measures and diagnoses the affect of the external stress stimuli using the FIT graphic. When a plant stress stimuli affects the plant with pathogens, water, herbicide or other stress, the fluorescence signatures, monitored one or more times daily, record in real-time the successive deterioration of photosynthesis and metabolic (chlorophyll yield) signatures.

The interactive operation, x-y selection and the Fluorescence-Intensity-Time (FIT) graphic enable the user to quantify with one measurement chlorophyll yield, photosynthetic efficiency and the plant's physiological response to plant stress. Fsubc, the chlorophyll yield at the x,y leaf location (FIG. 2) is the initial chlorophyll fluorescence quantum energy level. This fluorescence level is independent of the electron transport fluorescence or variable fluorescence. The two fluorescence signatures superimpose to give a graphic result. Fsubc is normally a step or pedestal curve. Fsubv, variable fluorescence, is the absorbed light emission that is not used in the plant's photochemical process. Fsubv is a transient response that peaks and quenches to a steady-state fluorescence value, Fsubs. The transient fluorescence variables are shown in FIG. 2.

The chlorophyll Fluorescence Intensity-Time signatures are the plant physiological responses to increasing plant stresses over time and recorded by the video imager and system software. After instantly reaching the Fsubc energy level, variable fluorescence increases to a maximum of Fsubp at tsubp, then quenches to the steady-state value, Fsubs. Increased plant stress stimuli will continue to shift the fluorescence maxima to increased values of peak-time. The quenching of Fsubp to Fsubs at tsubs continues to increase with longer tsubs, an indication of critical stress. FIG. 3 depicts fluorescence v. time curves for various responses of plant stress including; excellent photosynthetic efficiency (no transient fluorescence), (curve a) early and recoverable plant stress (curves b and c), advanced and recoverable plant stress (curve d in which Fsubs is greater than Fsubc) and critical non-recoverable plant stress (curve e, in which Fsubs is much greater than Fsubc). The special case of heat stress in plants is also shown (curve f). Heat stress causes the normal fluorescence energy step level of chlorophyll yield, Fsubc, to respond as a linearly increasing slope. When heat stress is imposed on early or advanced plant stress, the resulting multiple stress is a composite of the two independent responses (curve g).

FIG. 4 is a summary of FIT data examples of plant stresses as recorded by the CFIT system. FIG. 4A is a FIT of tomato with excellent photosynthetic efficiency. FIG. 4B is a FIT of early bean drought stress. FIGS. 4C and 4D are FIT data of the same plant with advanced stress. FIG. 4E shows the same plant recovered to an improved state 24 hours after watering. FIG. 4F is a graphic of the plant responding to environmental thermal stress. The first integral of intensity-time (right axis) quantifies the measurements. Fluorescence-Intensity-Time signatures for different species and plant stresses may be recorded and placed in the CFIT database as standards for comparison and as the user's plant stress library or database.

Field System Application Program Details

Start: The CFIT System Application Program is started by clicking on the icon or executing the "start.exe" instruction. The start instruction opens the program window with menus for File, Edit, Zoom, Process, and Palette.

New Capture Display Video Window: The display video window is selected by the File option of new capture (to acquire new data) or open (to open a stored image-data file from disk memory). The video image data, 150 sequential frames, is stored in the display video window. The video frame of 640 horizontal by 480 vertical is centered in the display video window. A right vertical scroll button positions the window and a lower horizontal scroll button scans or selects the video frames 1–150.

Video Data: The field system application program provides commands to the digital capture board in the computer image processor to start and buffer (store) the video data. A timing pulse at 100 msec intervals controls the video frame data output to 10 frames/sec to enable the processing and storing of real-time video image data in the video capture buffer. The start video data is activated by a radio button.

Activate False Color: The video data is false-colored to increase the visualization of fluorescence intensity data according to intensity values of 0–255 from the 8-bit analog-to digital data capture. The false colors of black to blue to white to red to green colors the increasing intensity data in equal bands. The Palette menu options the false color selection from gray-scale data.

Test Program: The Test Program is selected and started by a test radio button. The menu options different dark-adapt times with variable selection from 1 second to 60 min. When the test program is activated, the computer closes the shutter, preventing the continuous light source from irradiating the plant.

Test Capture: After the selected dark-adapt time runs out, the test program starts the video data to record the data, opens the shutter and stores 10 frames/sec for 15 seconds, 150 video frames into the display video window memory. The video data is also stored temporarily in the video capture buffer.

Save Data: The user selects the Save File radio button or Save from the file menu. The menu provides options to name and save the file to disk and to folder. When activated, the video data (the example is 640×480×150 matrix) is compressed and stored in the selected disk/folder database. After save, the video data remains in the display video window and in the video capture buffer.

Open File Display Video Window: The user selects the Open File from the File menu to retrieve a file from the disk/folder database. The display video window will activate if it is not already active under new capture. The File menu provides options to select the disk/folder and file name to select. After selection, the file is stored in the video capture buffer and the display video window. The user can open multiple files and save for simultaneous display in the display video window (for example 5). Each file can be independently operated with interactive graphics. This enables the visual and graphic measurement comparison of new file data to files in the database. A vertical scroll button enables the view of any of the multiple files.

Interactive Measurement Intensity-Time Graphics: In the display video window for either a new capture video or an open file video, a video data file of a test plant specimen is imaged and a video frame selected by the horizontal scroll to visualize (in false color) the fluorescence intensity. The video frames are horizontally scrolled to select the peak fluorescence by the false color intensity. After selecting the video frame to measure the intensity output, the user interactively selects any X-Y pixel location using the cursor. The location selects the intensity value from the X-Y-T matrix (data-cube). The values are buffered and plotted in the intensity-time graphic. The graphic is active in the display video window together with the video image frame and enables the user to interactively select and measure any X-Y pixels in the video frame image. The intensity-time values are graphed with Intensity on the Y-left axis and time on the X-axis. The integral $\int f(t)dt$ is graphed on the Y-right axis. The integral is the measure of area under the intensity curve and is a more refined measure of intensity-time. The two curves are plotted in different colors. The intensity is scaled 0–255 on the Y1 axis, time is scaled 0–15 seconds on the X-axis, and the integral is scaled from 0–max. on the Y-right axis.

Calibrate: A calibration of the light intensity at the video image plane by the CCD imager is necessary so that the incident light over the object field is modified to affect a balanced gain over the video-captured 640×480 image. To accomplish this, a calibration sheet is positioned in the interior of the CFIT at the correct working distance from the CCD imager. (The sheet may be held vertically at the interior side of the CFIT and positioned when manual calibration is deemed necessary.) With the light irradiated on the calibration sheet, a video image is captured. The X-Y intensity values for each X-Y pixel are read and tabled. After recording, a second read action measures a Δ value for each x-y pixel and compares to the maxima value in the center. (A design pre-setting has previously balanced and diffused light over the calibration sheet and established maxima values in the center.) The second read Δ values are added to the first X-Y pixel table, resulting in a balanced X-Y mapping that is calibrated to the X-Y center values. The result obtains X-Y pixel gains to obtain a uniform object image that accounts for real-time changes in variable lamp intensity. The calibration file is a module program that is run when the program is started or calibration is selected. The calibration data remains active and viable until imager settings are changed and re-calibration is required. A calibration bar may be positioned in the image field so that each captured image includes the reference measurement of real-time light intensity.

Auto-Gain: The pixel X-Y gain is set for each video image to be captured and is under control of the imager processor. The light intensity is measured (calibration bar) and a global gain value set and up-dated for the next cycle.

The up-date serves to continually monitor, and electronically alter, the video imaging gain to minimum pre-set conditions. (Scales and normalizes the low-level gains of certain spectral bands to higher gains).

Although specific features of the invention are shown in some drawings and not others, this is for convenience only as some feature may be combined with any or all of the other features in accordance with the invention.

Other embodiments will occur to those skilled in the art and are within the following claims:

What is claimed is:

1. A portable Chlorophyll Fluorescence Imaging Time (CFIT) system for use in determining plant health, comprising:

an enclosure for placement around a plant to be imaged in-situ;

means for controlling a light source and providing to the plant light of a desired wavelength range, to controllably irradiate the plant within the enclosure;

means for capturing chlorophyll fluorescence emitted from the plant both spatially and temporally, the means for capturing comprising an imaging sensor with a plurality of pixels defining an area sensor, to create an area fluorescence emission image of the plant, and means for storing in memory the output of the area sensor pixels over time, to form a data cube comprising the area fluorescence emission images saved over time;

means for allowing a user to select a pixel from those pixels for which data has been stored, and in response displaying for the user a graphic plot of the fluorescence intensity for the selected pixel over time and the first integral of said intensity-time; and means for analyzing the plotted fluorescence information to determine at least the chlorophyll yield and the plant's stress, wherein the shape of the fluorescence intensity curve and the value of the first integral indicate whether the plant is in excellent health, with a relatively flat curve and a relatively low first integral value, or the plant is in stress, with a curve having a peak and a greater first integral value.

2. A portable Chlorophyll Fluorescence Imaging Time (CFIT) system of claim 1 in which the area sensor captures energy in the red and new-infrared spectral hands.

3. A portable Chlorophyll Fluorescence Imaging Time (CFIT) system of claim 1 further comprising means for allowing a user to select a location in a saved image, and means for reporting to the user the measured fluorescence at the selected location.

4. A portable Chlorophyll Fluorescence Imaging Time (CFIT) system of claim 1 in which the light source comprises a lamp, and the means for controlling the light source comprises a shutter for controllably blocking light from the lamp from reaching the plant, and providing the lamp light to the plant.

5. A portable Chlorophyll Fluorescence Imaging Time (CFIT) system of claim 4 in which the means for controlling the light source further comprises means for controlling the shutter position.

6. A portable Chlorophyll Fluorescence Imaging Time (CFIT) system of claim 1 in which the light source comprises a plurality of light emitting diodes, and the means for controlling the light source comprises means for controlling the power to the light emitting diodes.

7. A portable Chlorophyll Fluorescence Imaging Time (CFIT) system for use in determining plant health, comprising:

an enclosure for placement around a plant to be imaged in-situ;

means for controlling a light source and providing to the plant light of a desired wavelength range, to controllably irradiate the plant within the enclosure;

an imaging sensor that captures energy in the red and near-infrared spectral bands with a plurality of pixels defining an area sensor to create an area fluorescence emission image of the plant, and means for storing in memory the output of the area sensor pixels over time, to form a data cube comprising the area fluorescence emission images saved over time, for capturing chlorophyll fluorescence emitted from the plant both spatially and temporally;

means for allowing a user to select a pixel from those pixels for which data has been stored, and in response displaying for the user a graphic plot of the fluorescence intensity for the selected pixel over time and the first integral of said intensity-time; and means for analyzing the plotted fluorescence information to determine at least the chlorophyll yield and the plant's stress, wherein the shape of the fluorescence intensity curve and the value of the first integral indicate whether the plant is in excellent health, with a relatively flat curve and a relatively low first integral value, or the plant is in stress, with a curve having a peak and a greater first integral value.

8. A portable Chlorophyll Fluorescence Imaging Time (CFIT) system for use in determining plant health, comprising:

an enclosure for placement around a plant to be imaged in-situ;

means for controlling a light source and providing to the plant light of a desired wavelength range, to controllably irradiate the plant within the enclosure;

means for capturing chlorophyll fluorescence emitted from the plant both spatially and temporally;

means for allowing a user to select a pixel from those pixels for which data has been stored, and in response displaying for the user a graphic plot the fluorescence intensity for the selected pixel over time and the first integral of said intensity-time; and means for analyzing the plotted fluorescence information, to determine at least the chlorophyll yield and the plant's stress, wherein the shape of the fluorescence intensity curve and the value of the first integral indicate whether the plant is in excellent health, with a relatively flat curve and a relatively low first integral value, or the plant is in stress, with a curve having a peak and a greater first integral value.

9. A portable Chlorophyll Fluorescence Imaging Time (CFIT) system of claim 8 in which the means for capturing includes an imaging sensor with a plurality of pixels defining an area sensor, to create an area fluorescence image of the plant.

10. A portable Chlorophyll Fluorescence Imaging Time (CFIT) system of claim 9 in which the means for capturing further includes means for storing in memory the output of the sensor pixels over time, to form a data cube comprising the area fluorescence emission images saved over time.

11. A portable Chlorophyll Fluorescence Imaging Time (CFIT) system of claim 8 in which the area sensor captures energy in the red and near-infrared spectral bands.

12. A portable Chlorophyll Fluorescence Imaging Time (CFIT) system of claim 8 further comprising means for allowing a user to select a location in a saved image, and means for reporting to the user the measured fluorescence at the selected location.

13. A portable Chlorophyll Fluorescence Imaging Time (CFIT) system of claim 1 in which the light source comprises a lamp, and the means for controlling the light source comprises a shutter for controllably blocking light from the lamp from reaching the plant, and providing the lamp light to the plant.

14. A portable Chlorophyll Fluorescence Imaging Time (CFIT) system of claim 13 in which the means for controlling the light source further comprises means for controlling the shutter position.

15. A portable Chlorophyll Fluorescence Imaging Time (CFIT) system of claim 8 in which the light source comprises a plurality of light emitting diodes, and the means for controlling the light source comprises means for controlling the power to the light emitting diodes.

* * * * *